(12) United States Patent
Seifert

(10) Patent No.: US 7,974,710 B2
(45) Date of Patent: Jul. 5, 2011

(54) GUIDE CATHETERS FOR ACCESSING CARDIAC SITES

(75) Inventor: Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 801 days.

(21) Appl. No.: 11/116,802

(22) Filed: Apr. 28, 2005

(65) Prior Publication Data

US 2006/0247751 A1    Nov. 2, 2006

(51) Int. Cl.
*A61N 1/05* (2006.01)
(52) U.S. Cl. .................................. 607/126; 607/120
(58) Field of Classification Search ............ 607/126, 607/122; 606/129
See application file for complete search history.

(56) References Cited

U.S. PATENT DOCUMENTS

| | | | |
|---|---|---|---|
| 3,835,864 A | 9/1974 | Rasor et al. | |
| 4,233,992 A | 11/1980 | Bisping | 128/785 |
| 4,506,680 A | 3/1985 | Stokes | 128/786 |
| 4,577,642 A | 3/1986 | Stokes | 128/784 |
| 4,606,118 A | 8/1986 | Cannon et al. | 29/825 |
| 4,711,251 A | 12/1987 | Stokes | 128/784 |
| 4,815,478 A | 3/1989 | Buchbinder et al. | 128/772 |
| 5,003,990 A | 4/1991 | Osypka | 128/772 |
| 5,246,014 A | 9/1993 | Williams et al. | 607/122 |
| 5,304,218 A | 4/1994 | Alferness | 607/122 |
| 5,827,216 A * | 10/1998 | Igo et al. | 604/21 |
| 5,873,842 A | 2/1999 | Brennen et al. | 600/585 |
| 5,897,584 A | 4/1999 | Herman | 607/122 |
| 5,902,324 A | 5/1999 | Thompson et al. | 607/9 |
| 5,902,331 A | 5/1999 | Bonner et al. | 607/122 |
| 5,903,324 A | 5/1999 | Lyons et al. | 348/845.3 |
| 5,987,746 A | 11/1999 | Williams | 29/876 |
| 6,110,163 A | 8/2000 | Voda | 604/523 |
| 6,132,456 A | 10/2000 | Sommer et al. | 607/127 |
| 6,146,338 A | 11/2000 | Gardeski et al. | 600/585 |
| 6,185,464 B1 | 2/2001 | Bonner et al. | 607/119 |
| 6,190,349 B1 * | 2/2001 | Ash et al. | 604/43 |
| 6,280,433 B1 | 8/2001 | McIvor et al. | 604/524 |
| 6,379,346 B1 | 4/2002 | McIvor et al. | 604/524 |
| 6,408,214 B1 | 6/2002 | Williams et al. | 607/122 |
| 6,659,981 B2 * | 12/2003 | Stewart et al. | 604/164.02 |
| 2004/0039371 A1 | 2/2004 | Tockman et al. | 604/528 |
| 2004/0102830 A1 | 5/2004 | Williams | 607/125 |
| 2004/0116848 A1 | 6/2004 | Gardeski et al. | 604/95.01 |
| 2004/0116878 A1 | 6/2004 | Byrd et al. | 604/263 |

OTHER PUBLICATIONS

U.S. Appl. No. 10/688,229, filed Oct. 17, 2003, entitled "Medical Electrical Fixation" to Hess et al.

* cited by examiner

*Primary Examiner* — Carl H. Layno
*Assistant Examiner* — Tammie K Heller

(57) ABSTRACT

Guide catheters for facilitating implantation of cardiac leads for applying electrical stimulation to and/or sensing electrical activity of the heart through one or more electrodes positioned at an implantation site within a heart chamber or cardiac vessel adjacent a heart chamber. Such a cardiac lead has low torqueability and pushability through a pathway to enable attachment of the cardiac lead at the implantation site. The catheter body comprises a delivery lumen to introduce a small diameter cardiac lead and a guide lumen to receive a guide tool to locate the catheter body distal end at the implantation site. The small diameter lumen within a small diameter guide tube extends distally from the delivery exit port of the delivery lumen. The catheter body is shaped to bias the delivery lumen exit port toward the heart.

23 Claims, 7 Drawing Sheets

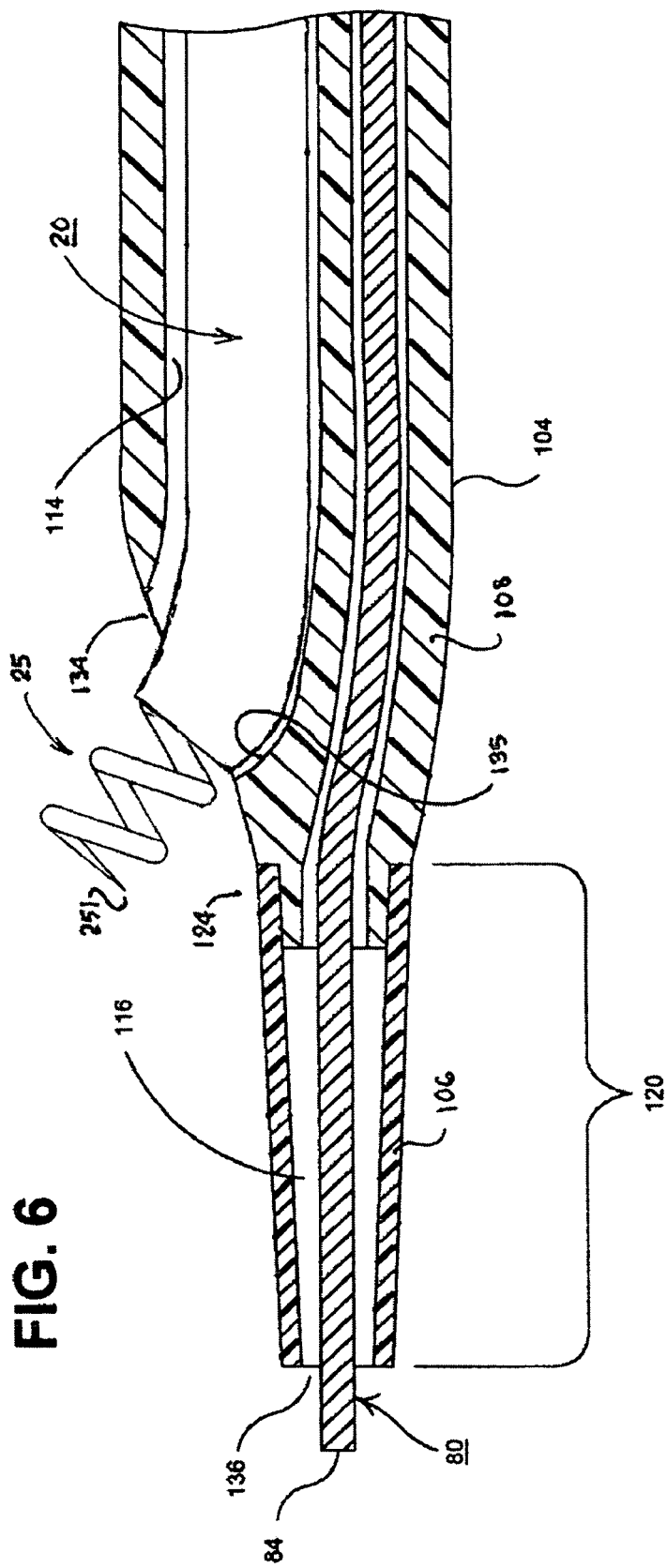

GUIDE CATHETERS FOR ACCESSING CARDIAC SITES

TECHNICAL FIELD

The present invention relates to bilumen guide catheters for introduction and implantation of cardiac leads for applying electrical stimulation to and/or sensing electrical activity of the heart or the introduction of other medical instruments and materials into cardiac vessels, particularly the coronary sinus (CS) and vessels branching therefrom.

BACKGROUND

Implantable permanent and temporary medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, the electrodes of epicardial or endocardial cardiac leads are affixed against the epicardium or endocardium, respectively, or inserted therethrough into the underlying myocardium of the heart wall.

It has become possible to reduce endocardial lead body diameters from 10 to 12 French (3.3 to 4.0 mm) down to 2 French (0.66 mm) presently through a variety of improvements in conductor and insulator materials and manufacturing techniques. The lead bodies of such small diameter, 2 French, endocardial leads are formed without a lumen that accommodates use of a stiffening stylet to assist in implantation.

These small diameter endocardial pacing and cardioversion/defibrillation leads are advantageously sized to be advanced into the coronary sinus to locate the distal electrode (s) adjacent to the left atrium or into coronary veins branching from the coronary sinus to locate the distal electrode(s) adjacent to the left ventricle. The distal end of such a coronary sinus lead is advanced through the superior vena cava, the right atrium, the valve of the coronary sinus, the coronary sinus, and, if employed to pace or sense the left ventricle, into a cardiac vein branching from the coronary sinus.

Typically, such small diameter endocardial leads are formed with an active fixation helix that extends distally and axially in alignment with the lead body to a sharpened distal tip and that has a helix diameter substantially equal to the lead body diameter. The fixation helix does not necessarily increase the overall diameter of the endocardial lead and is relatively robust, once the helix is screwed into the myocardium. Typically, but not necessarily, the fixation helix is electrically connected to a lead conductor and functions as a pace/sense electrode. In some cases, the lead body encloses one or more helical coiled or stranded wire conductor and lacks a lumen.

The lead bodies of such small diameter endocardial screw-in leads are so supple and flexible that it is difficult to rotate the lead distal end by application of rotary torque to the lead proximal end unless the lead body remains relatively straight and not confined by contact with vessel walls. This diminished "torqueability" prevents the rotation of the fixation helix at the lead distal end or renders the rotation unreliable once the lead body is advanced through a tortuous pathway and confined by contact against the vessel walls. To the degree that rotation torque can be transmitted from the lead proximal end to the lead distal end, the active fixation helix at the lead distal end can be over-rotated and screwed through the myocardium or under-rotated and not screwed into the myocardium sufficiently. In addition, such lead bodies also possess little if any column strength and lack "pushability", that is the ability to advance the lead distal end axially when the lead proximal end is pushed axially, particularly when the lead body extends through the tortuous transvenous pathway. Thus, it has been found necessary to use implantation instruments or tools that compensate for the lack of pushability and torqueability of the lead body.

Once the implantation site is reached in coronary vasculature, it is difficult to aim the distal fixation mechanism toward myocardial tissue, and the fixation mechanism may inadvertently be aimed at and deployed outside the myocardium. The pace/sense electrodes may not be in intimate contact with excitable cardiac tissue, resulting in unduly high stimulation thresholds and diminished sensing. Fixation may be achieved temporarily, but fixation may be lost over time resulting in dislodgement of the pace/sense electrode(s). The fixation mechanism may perforate through a coronary vessel wall into the pericardial space resulting in perforation of the vessel.

SUMMARY

The present invention provides a multi-lumen guide catheter that can be employed to introduce and locate an electrode of a cardiac lead at a desired implantation site in a coronary blood vessel that satisfies these needs. The multi-lumen guide catheter includes an elongated, multi-lumen catheter body having a catheter body proximal end coupled to a handle or hub and extending to the catheter body distal end. The multi-lumen guide catheter body includes at least one relatively large diameter delivery lumen and a relatively small diameter guide lumen that extend side-by-side through a proximal portion of the guide catheter body. A distal portion of the guide catheter body encloses and extends the guide lumen to a guide lumen exit port distal to a delivery lumen exit port at the junction of the proximal and distal portions of the guide catheter body. A guide tool is inserted into or received within the guide lumen.

At least a portion of the guide catheter is shaped to preferentially urge the delivery catheter lumen exit port toward the vessel wall and the underlying heart and away from the pericardium and pericardial space during advancement of the guide catheter body through coronary vessels. For example, the guide catheter body is shaped in one or more segment thereof such that the delivery lumen exit port is oriented or biased inward toward the myocardium and not outward toward the pericardial sac or pericardium as the guide catheter is advanced through a coronary blood vessel that extends over the epicardium of the heart. This orientation of the delivery lumen exit port enables advancement of an active fixation mechanism of a cardiac lead out of the delivery lumen exit port and through the vessel wall and epicardium into the myocardium. The guide tool can be retracted through the guide lumen before or after advancement and fixation of the active fixation mechanism, and the guide catheter can then be withdrawn over the lead body without disturbing the fixation.

In use, the cardiac lead is fitted into the delivery lumen, and the guide catheter body is advanced through the tortuous pathway to dispose the delivery lumen exit port facing toward the vessel wall overlying the selected fixation site. The cardiac lead is advanced distally to extend the distal fixation mechanism through the delivery lumen exit port. The fixation mechanism is actuated to affix the fixation mechanism through the vessel wall into myocardial tissue, and the guide catheter body and guide tool within the guide lumen are retracted from the coronary vasculature and from the body.

In one embodiment, the delivery lumen exit port is formed through a catheter body sidewall. At least a segment of the guide catheter body is shaped to preferentially urge the delivery catheter lumen exit port toward the vessel wall and the underlying heart and away from the pericardium during advancement of the guide catheter body through coronary vessels. The distal fixation mechanism of the cardiac lead is advanced out of the delivery lumen exit port toward the heart and advantageously fixed into the myocardium.

In a variation of this embodiment, the multi-lumen guide catheter body includes two delivery lumens extending through the proximal portion of the catheter body to two delivery lumen exit ports formed through the catheter body sidewall spaced apart longitudinally from one another. The shaped guide catheter body urges the delivery lumen exit ports toward the heart. Advantageously, two cardiac leads can be advanced to two spaced apart sites within the coronary vasculature, and the distal fixation mechanisms can be independently advanced out of each delivery lumen exit port toward the heart and fixed into the myocardium.

In certain embodiments, the guide catheter body is reduced in diameter in the distal portion extending between the delivery lumen exit port and the guide lumen exit port and at the catheter body distal end, also referred to herein as a "distal leader". Consequently, the small diameter distal leader can be advanced readily over a guide wire inserted into the guide lumen through twists and turns of the tortuous pathway and thereby guides the advancement of the larger diameter proximal segment of the catheter body. The small diameter distal leader can also be advanced deeply into narrow pathways or passages to dispose the more proximal delivery lumen exit port at a desired implantation site.

The guide tool includes a guide wire that has already been advanced through the tortuous pathway. However, the guide tool can be a removable stiffening stylet that can be manually shaped to impart a bend in the distal segment of the guide catheter and can be inserted or withdrawn from the guide lumen, or (in certain embodiments) a pull wire coupled at the distal end of the guide lumen and extending proximally through the guide lumen. The guide lumen exit port can be left open to provide for use either with a guide wire in an over-the-wire introduction or with a removable stiffening stylet. Alternatively, the guide lumen exit port can be closed for use with a removable stiffening stylet or a fixed pull wire. The stiffening stylet can be provided with a selectable shape to enable advancement through the tortuous pathway or disposition of the delivery lumen exit port and at a selected implantation site. Or, a steerable stylet having a distal segment in which a bend can be selectively imparted or removed by manipulation of a proximal handle can advantageously be employed to impart a bend in the distal leader of the catheter body to steer it through bends and turns of a tortuous pathway.

The guide catheters and methods of the present invention advantageously simplify introduction of cardiac leads that lack a lumen for receiving a stiffening stylet and lack sufficient column strength to be pushed to a desired implantation site. The implantation sites include any selected implantation sites of the coronary sinus and the cardiac veins descending from the coronary sinus accessed through a transvenous pathway.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Aspects and features of the present invention will be readily appreciated as the present invention becomes better understood by reference to the following detailed description when considered in connection with the accompanying drawings, in which like reference numerals designate like parts throughout the figures thereof and wherein:

FIG. 6 is a cross-section view taken along lines 6-6 in FIG. 4 depicting the shape of the delivery catheter lumen exit port to urge the distal fixation helix of the cardiac lead of FIG. 2 toward the vessel wall and the underlying heart and away from the pericardium and pericardial space during advancement of the guide catheter body through coronary vessels depicted in FIG. 1;

Figure 1:
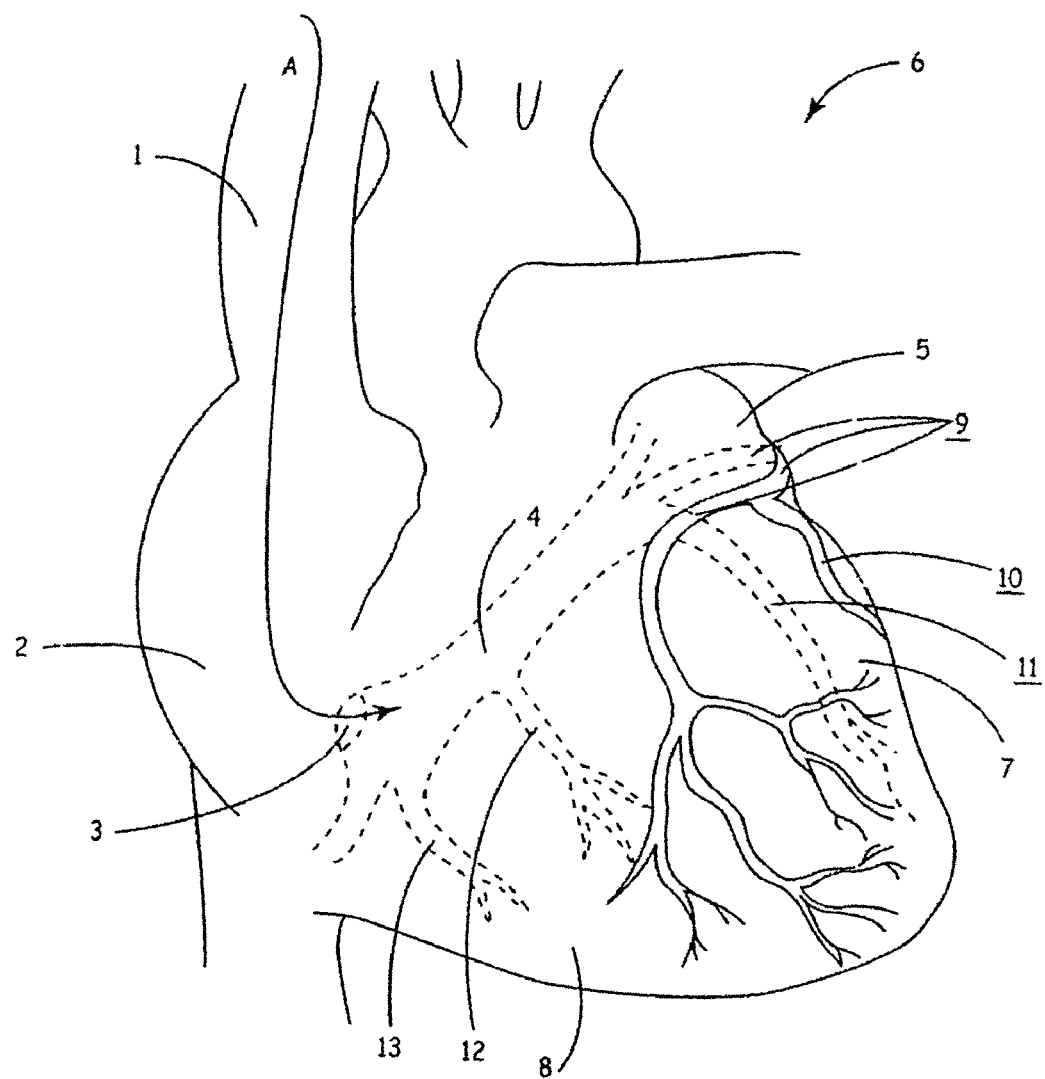
FIG. 1 is a schematic diagram of a heart from an anterior perspective illustrating the coronary venous system about an epicardial surface of the heart, including dashed lines depicting a portion of coronary venous system on an opposite, posterior epicardial surface of the heart.

The drawing figures are not necessarily to scale.

DETAILED DESCRIPTION OF PREFERRED EMBODIMENTS

In the following detailed description, references are made to illustrative embodiments for carrying out the invention. It is understood that other embodiments may be utilized without departing from the scope of the invention. The invention and its preferred embodiments may be employed in implantation of unipolar, bipolar or multi-polar, endocardial, cardiac pacing leads, cardioversion/defibrillation leads or monitoring leads having one or more pace/sense electrode(s) or sense electrode(s), respectively, at or adjacent the distal lead end and an active fixation mechanism that is to be affixed into the myocardium. Moreover, other sensors for sensing a physiologic parameter may be incorporated into the lead body. An insulated electrical conductor extending proximally through the lead body to connector element of a lead proximal end connector assembly is coupled to each such pace/sense electrode, sense electrode, cardioversion/defibrillation electrode and sensor. The proximal connector assembly is adapted to be coupled to the connector assembly of an external medical device, including an external pacemaker or monitor, or an implantable medical device, including an IPG for pacing, cardioversion/defibrillation (or both) or an implantable monitor. Therefore, it will be understood that the arrangement for introduction of a cardiac lead of the present invention can be employed to introduce permanently implantable and temporary cardiac leads of any of these types, particularly within the coronary vasculature.

The multi-lumen guide catheters and methods of the present invention are particularly useful in introducing such small diameter cardiac leads that are devoid of a stylet lumen and are so flexible and possess such low column strength, rigidity, pushability and torqueability that the lead distal end cannot be advanced transvenously and positioned at the desired implantation site without assistance. Moreover, one particular use of the arrangement of the present invention is to introduce such cardiac leads that are formed using stranded wire conductor(s) within a lead body diameter of about 0.010-0.026 inches of the type described in the commonly assigned U.S. Pat. No. 5,246,014, herein incorporated by reference in its entirety. The lead body outer diameter is minimized by use of such conductors and by eliminating the lumen for receiving a stiffening stylet. However, the arrangement of the present invention can also be employed to introduce cardiac leads that employ coiled wire conductors with or without a lumen for receiving a stiffening stylet. In the latter case, the stiffening stylet need not be used to achieve the introduction.

FIG. 1 is a schematic diagram of a heart 6 from an anterior perspective illustrating a coronary venous system about an epicardial surface, including dashed lines depicting a portion of coronary venous system on an opposite, posterior surface of the heart 6. FIG. 1 also illustrates a pathway, defined by arrow 'A', which may be followed in order to place a cardiac lead within CS 4, extending from a venous access site (not shown) through the superior vena cava (SVC) 1 into the right atrium (RA) 2 of heart 6 and from the RA 2 into the CS 4 through a coronary sinus ostium (CS Os) 3.

As illustrated in FIG. 1, the coronary venous system of a heart 6 includes the CS 4 and vessels branching therefrom including the middle cardiac vein (MCV) 13, the posterior cardiac vein (PCV) 12, the posterior-lateral cardiac vein (PLV) 11, the great cardiac vein (GCV) 9, and the lateral cardiac vein (LCV) 10 all branching away from the CS 4. Generally speaking, the distal portion of the CS 4 and the branching vessels including at least portions of the MCV 13, PCV 12, the PLV 11, the GCV 9, and the LCV 10 overlie the or are embedded within the epicardium that defines outer surface of the heart 6 and encases heart muscle or myocardium. Portions of the epicardium are spaced from a surrounding pericardial sac or pericardium (not shown), whereby a pericardial space surrounds the spaced epicardium of heart 6. Thus, the vessel walls of the distal portion of the CS 4 and the branching vessels including at least portions of the MCV 13, PCV 12, the PLV 11, the GCV 9, and the LCV 10 are partially exposed to the pericardial space or adhered to the pericardium and are partially embedded against the underlying myocardium. For convenience of terminology, the vessel walls that are disposed toward the pericardium are referred to as disposed "away from the heart", whereas the vessel walls that are disposed toward the myocardium are referred to as disposed "toward the heart".

In patients suffering from heart failure, a CS lead of the types described above is advanced through the pathway "A" extending through the SVC 1 and RA 2 into the CS 4 to dispose one or a pair of distal pace/sense electrodes at an LV site(s) within one of the vessels branching from the CS 4. An RV lead is advanced through the SVC 1, the RA 2, the tricuspid valve, and the distal pace/sense electrode(s) is affixed at an RV pace/sense site(s) of the RV 8, e.g., in the RV apex or along the septum separating the RV and LV chambers. The RV lead can take any of the functions known in the art preferably having an active or passive fixation mechanism.

The proximal connectors of the CS lead and the RV lead are coupled to a connector header of a pacing IPG or an ICD IPG (not shown) implanted subcutaneously. The IPG is capable of sensing and processing cardiac signals detected at the pace/sense site(s) to provide synchronized RV and LV pacing at the pace/sense sites as needed. The pacing and sensing functions of such an IPG that provides synchronous activation of the RV 8 and LV 7 in order to improve the hemodynamic output of the heart 6 are disclosed in commonly assigned U.S. Pat. No. 5,902,324, for example, and are embodied in the MEDTRONIC® InSync Marquis™ ICD IPG, for example.

Hemodynamic output is enhanced when the CS pace/sense electrode(s) site is selected within a late activated region of LV 7. Late activated regions of the LV 7 are found within the myocardium underlying the PLV 11, the LCV 10, the GCV 9, or the CS 4 near a junction with the GCV 9. Moreover, pacing and sensing functions are optimized when the pace/sense electrode(s) are disposed in intimate contact with excitable myocardial tissue.

The lead body of a permanent or temporary cardiac lead typically includes one or more insulated conductive wire surrounded by an insulating outer sheath. Each conductive wire couples a proximal lead connector element with a distal stimulation and/or sensing electrode. Temporary and permanent cardiac leads having a single stimulation and/or sensing electrode at the lead distal end, a single conductor, and a single connector element are referred to as unipolar cardiac leads. Temporary and permanent cardiac leads having two or more stimulation and/or sensing electrodes at the lead distal end, two or more respective conductors, and two or more respective connector elements are referred to as bipolar lead or multi-polar leads, respectively.

Figure 2:
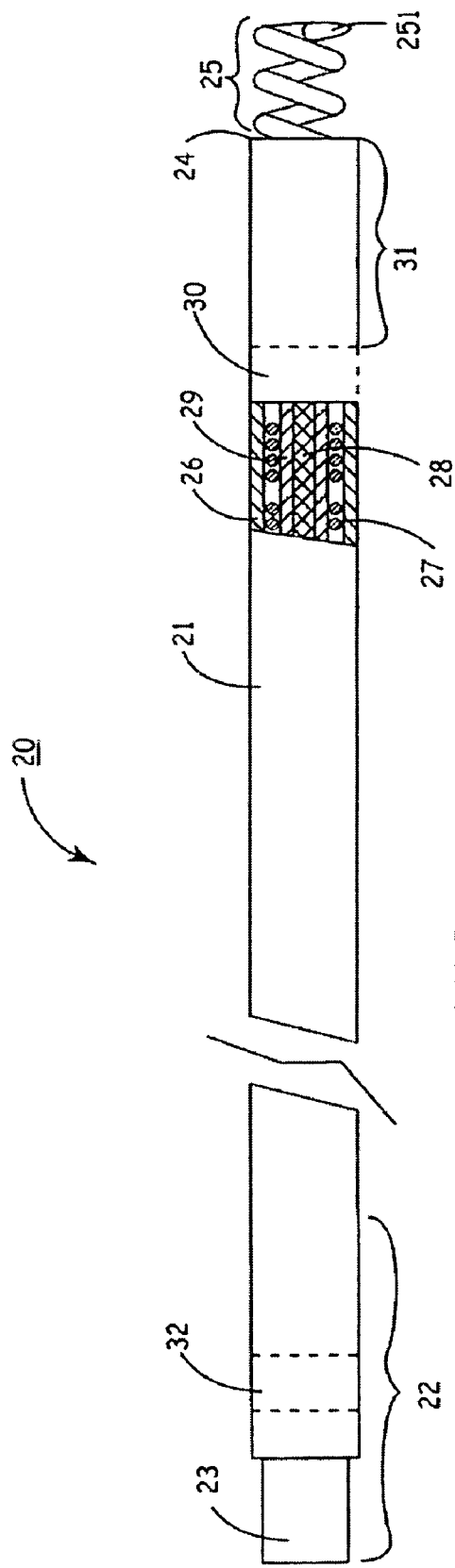
FIG. 2 is a plan view, in partial exposed section, of a typical pacing lead that can be introduced and affixed in the coronary venous system employing a bitumen guide catheter and method of the present invention.
Figure 3:
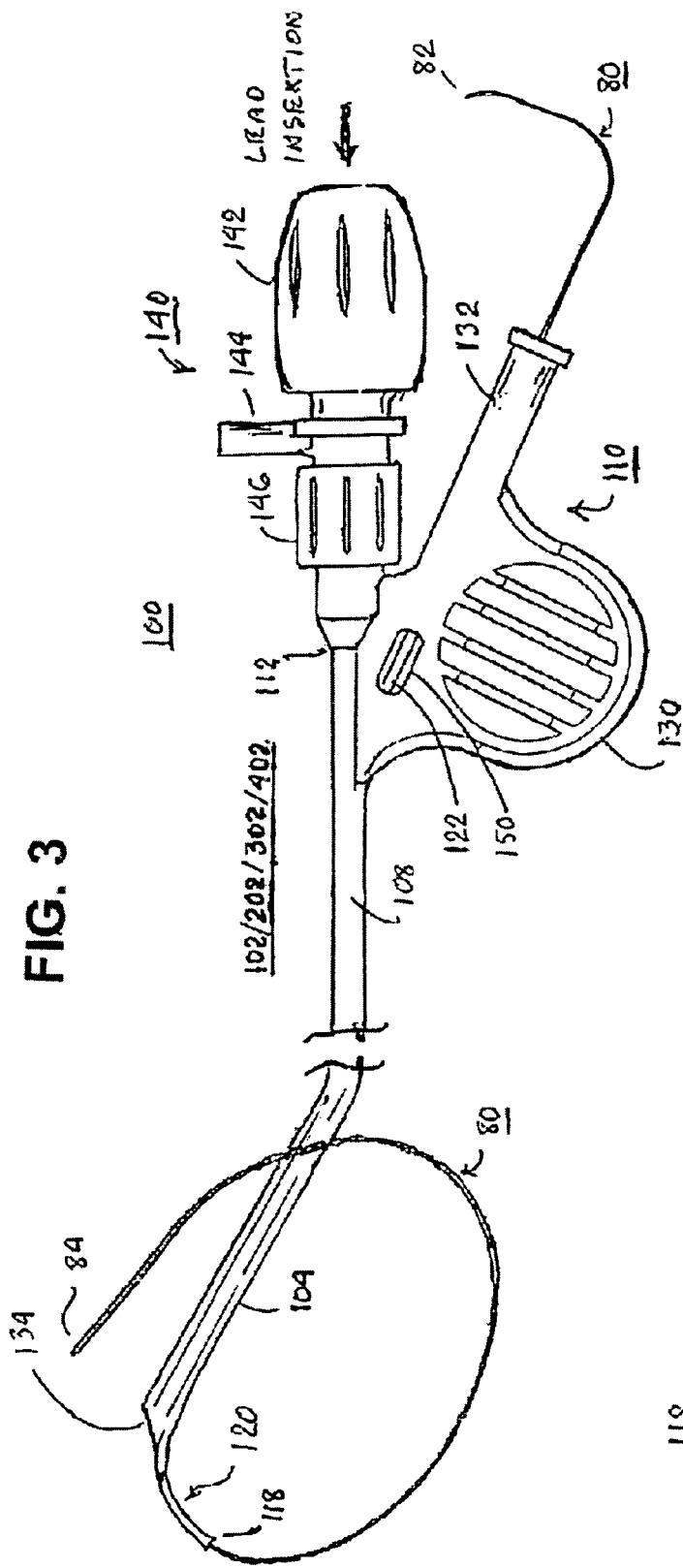
FIG. 3 is a plan view of a guide wire and an over-the-wire bilumen guide catheter in accordance with a first embodiment of the invention adapted to be advanced through the tortuous pathway from outside the patient's body to the implantation sites illustrated in FIG. 1, for example, over the guide wire.

A typical example of an active fixation cardiac lead 20 that can be introduced through a bilumen guide catheter of the present invention advanced through pathway "A" and employed as a CS lead is schematically illustrated in FIG. 2. The cardiac lead 20 can also be introduced as described above into the RV to function as an RV lead. The cardiac lead 20 has an elongated lead body 21 that extends between a proximal connector 22 and a distal end 24. A helical fixation element or helix 25 having a sharpened piercing tip 251 extends distally from lead body distal end 24. Pacing lead 20 is essentially iso-diametric along its length, with an outer diameter of lead body 21 and fixation helix 25 between approximately 1 French (0.33 mm) to 3 French (1.00 mm). Since lead body 21 does not include an inner lumen, the outer diameter of lead body 21 is reduced.

Lead body 21 is constructed of a stranded conductive or non-conductive filament cable 28 disposed within an inner sheath lumen of an inner sheath 29, which in turn extends through the coil lumen of a coil 27. The assembly of the coil 27, inner sheath 29, and cable 28 is fitted through an outer sheath lumen of an outer sheath 26.

Coil 27 is formed of any bio-stable and biocompatible material that is sufficiently stiff to provide adequate torque transfer from proximal connector assembly 22 to fixation element 25 at distal end 24 of cardiac lead 20. When coil 27 functions as a lead conductor, coil 27 is preferably formed of single or multiple wire filars made of MP35-N alloy, well known in the art, or any other bio-stable and biocompatible material that is capable of reliably conducting electrical current after having been subjected to numerous, repeated bending and torsional stresses.

Inner cable 28 is formed from synthetic filaments or conductive metallic wires, when inner cable functions as a lead conductor. The proximal and distal ends of inner cable 28 are coupled to connector pin 23 or within connector assembly 22 and fixation helix 25, respectively, to provide tensile strength to lead body 21.

Outer sheath 26 is formed of either a silicone rubber or polyurethane, well known in the art, or any other flexible, bio-stable and biocompatible, electrically insulating, polymer material. Inner sheath 29 is similarly formed of a bio-stable and biocompatible flexible polymer coating or tube that protects inner cable 28 from mechanical stresses or degradation and electrically insulates inner cable 28 from contact with wire coil 27. Inner sheath 29 can be formed of flexible, bio-stable and biocompatible electrically insulating materials known in the art, including silicone rubber compounds, polyurethanes, and fluoropolymers.

In both unipolar and bipolar cardiac lead embodiments, the proximal connector assembly 22 includes a connector pin 23 that is typically electrically connected with the distal fixation helix 25 when the distal fixation helix 25 functions as a pace/sense electrode. In a bipolar cardiac lead embodiment, the proximal connector assembly 22 includes a connector ring 32 (shown with dashed lines) that is electrically coupled to a ring-shaped pace/sense electrode 30 (shown with dashed lines) supported by outer sheath 26 proximal to fixation helix 25. The connector assembly 22 is shaped to be inserted into a bore of a connector block of the connector header of an IPG as described above to make an electrical connection between the distal pace/sense electrode(s) and IPG sensing and/or pacing pulse generating circuitry. Ring-shaped pace/sense electrode 30 is preferably formed of a platinum alloy but other materials may also be used, including but not limited to such materials as palladium, titanium, tantalum, rhodium, iridium, carbon, vitreous carbon and alloys, oxides and nitrides of such metals or other conductive or even semi-conductive materials. Of course, some materials are incompatible with others and may not be effectively used together. The limitations of specific materials for use with others are well known in the art.

The fixation helix 25 is adapted to be screwed into the myocardium, as described below, by rotation of lead body 21 from the proximal connector assembly 22 when piercing tip 251 is advanced to and oriented toward a fixation site. When fixation helix 25 functions as a pace/sense electrode, as in alternate embodiments described above, fixation helix 25 is preferably formed of a platinum iridium alloy, although it is understood that other biocompatible and bio-stable materials may also be used, including but not limited to such materials as palladium, titanium, tantalum, rhodium, carbon, vitreous carbon and alloys, oxides and nitrides of such metals or other conductive or even semi-conductive materials well known in the art.

In a unipolar embodiment of cardiac lead 20, the inner cable 28 is nonconductive, a proximal end of coil 27 is coupled to connector pin 23, and a distal end of coil 27 is coupled to the proximal end of fixation helix 25. The proximal and distal ends of coil 27 are welded or crimped to the connector pin 23 and fixation helix 25, respectively, using common welding or crimping techniques known in the art. The proximal and distal ends of inner cable 28 are crimped to the connector pin 23 or connector assembly 22 and fixation helix 25, respectively, using common welding or crimping techniques known in the art.

In an alternate unipolar embodiment wherein the inner cable is nonconductive, helix fixation element 25 simply provides fixation and does not function as a pace/sense electrode. The proximal end of coil 27 is coupled to connector pin 23, and the distal end of coil 27 is coupled to the ring-shaped pace/sense electrode 30 incorporated coaxially about a distal portion of lead body 21. The spacing 31 between ring-shaped pace/sense electrode 30 and fixation helix 25 is less than approximately 0.02 inches, in order to locate ring-shaped pace/sense electrode 30 close enough to a fixation site for tissue contact when fixation helix 25 is fixed into the myocardium.

In a further alternate unipolar embodiment of cardiac lead 20, inner cable 28 is electrically conductive, and the proximal and distal cable ends are electrically coupled by crimping or welding or other known techniques to connector pin 23 and helix fixation element 25, respectively. Inner sheath 29 electrically insulates inner cable 28 from coil 27, which acts only as a structural element to provide torsional stiffness to lead body 21. Alternatively, the proximal and distal ends of the conductive inner cable 28 and the wire coil 27 can be electrically connected together to provide a redundant unipolar lead conductors. Conductive inner cable 28 is preferably formed from wire strands or filaments made of MP35-N alloy, well known in the art, or any other bio-stable and biocompatible material that is capable of reliably conducting electrical current after having been subjected to numerous, repeated bending and torsional stresses.

In a bipolar embodiment of cardiac lead 20, both coil 27 and inner cable 28 are lead conductors as described above, that are electrically insulated from one another by inner sheath 29. In this embodiment, the proximal and distal ends of coil 27 are electrically and mechanically coupled by crimping or welding to the connector ring 32 and the ring-shaped pace/sense electrode 30, respectively. The proximal and distal ends of the inner cable 28 are electrically and mechanically coupled by crimping or welding to connector pin 23 and distal fixation helix 25, respectively. The spacing 31 between ring-shaped pace/sense electrode 30 and fixation helix 25 is between approximately 0.2 inches and 0.4 inches, a range well known in the pacing art for inter-electrode bipolar pace/sense electrode spacing.

The exemplary active fixation cardiac lead 20 can also be formed having an elongated cardioversion/defibrillation (C/D) electrode extending proximally a predetermined distance along the outer sheath 21 from a C/D electrode distal end located proximal to distal lead end 24. The proximal and distal ends of the wire coil 27 would be electrically and mechanically coupled to the connector ring 32 and the elongated C/D electrode, respectively. The proximal and distal ends of the inner cable 28 would be electrically and mechanically coupled by crimping or welding to connector pin 23 and distal fixation helix 25, respectively.

A means for steroid elution may be incorporated into any of the aforementioned embodiments of the exemplary active fixation cardiac lead 20 near distal end 24. Such steroid elution means may take the form of a monolithic controlled release device (MCRD), constructed, for example, from silicone rubber and loaded with a derivative of dexamethasone, such as the water-soluble steroid dexamethasone sodium phosphate. MCRD construction and methods of fabrication are found in commonly assigned U.S. Pat. Nos. 4,506,680, 4,577,642, 4,606,118, and 4,711,251. Alternatively a steroid coating containing a no more than sparingly water-soluble steroid such as beclomethasone diproprionate or dexamethasone acetate may be applied to surfaces of ring-shaped pace/sense electrode 30 and/or fixation helix 25. A steroid coating composition and method of application is found in commonly assigned U.S. Pat. No. 5,987,746. The steroid coating may be applied directly to surfaces or portions of surfaces preserving structural integrity of ring-shaped pace/sense electrode 30 and/or fixation helix 25 and taking up less space than an MCRD.

Such an exemplary active fixation cardiac lead 20 can be employed advantageously as a CS lead through the use of the bilumen guide catheters of the present invention advanced through the pathway "A" of FIG. 1 to locate the fixation helix 25 at a fixation site in the coronary vasculature and to aim the helix tip 251 toward the heart before the connector assembly 22 is rotated to screw the fixation helix 25 through the vessel wall and into the myocardium.

The guide catheters of the present invention enable the implantation of a small diameter lead body 21 in the range of 1 French (0.33 mm) to 3 French (1.00 mm), but it will be understood that the over-the-wire guide catheters can be sized to facilitate implantation of larger diameter lead bodies exceeding 3 French in diameter. It will be understood that the guide catheters and methods of use disclosed herein can be employed to introduce and secure any form of distal fixation hooks or fixation helices either extending distally like distal fixation helix 70 or laterally from the lead body in the manner of those distal fixation helices disclosed in U.S. Pat. Nos. 3,835,864 and 4,233,992, for example. It will be understood that other active fixation cardiac leads having differing shaped fixation mechanisms, e.g., barbs or prongs or pins, can also be advantageously employed with the bitumen guide catheters of the present invention. For example, the guide catheters of the present invention can be employed to locate the fixation mechanism at a fixation site in the coronary vasculature and to aim a fixation mechanism toward the heart before the proximal connector assembly or a further device is activated or manipulated to advance and drive the fixation mechanism through the vessel wall and into the myocardium.

Turning to FIGS. 3-6, a first embodiment of an exemplary elongated bilumen guide catheter 100 adapted to be used with a guide tool including a guide wire 80, for example, is illustrated. The guide wire 80 extends between a guide wire proximal end 82 and a guide wire distal end 84 and is adapted to be advanced through the tortuous pathway "A" from outside the patient's body to the implantation sites illustrated in FIG. 1, for example. The bilumen guide catheter 100 depicted in FIG. 3 includes an elongated catheter body 102 extending from a catheter body proximal end 112 joined with proximal handle or hub 110 to a catheter body distal end 118. The elongated catheter body 102 has a length of about 25 cm to 120 cm depending upon the length of the selected pathway from the skin incision through the patient's body to the implantation site. The catheter body 102 further includes a proximal portion 108 and a distal portion or leader 120 that are joined together at junction 124 as shown in FIG. 6. The distal leader 120 may have a length on the order of about 10 mm to about 25 mm.

The bitumen guide catheter 100 receives a small diameter cardiac lead, e.g., cardiac lead 20, during the advancement of the catheter body 102 through the tortuous pathway "A" and facilitates fixation of the distal helix 25 at the selected implantation site as shown in FIG. 6. The advancement is facilitated by advancement of the small diameter distal leader 120 of the guide catheter 100 over the previously placed guide wire 80 past the selected implantation site.

The catheter body 102 therefore encloses a delivery lumen 114 extending between a guide lumen entry port at the catheter body proximal end 112 within the hub 110 and the catheter body distal end 118. The delivery lumen diameter is sized to receive the guide wire 80 inserted therein to aid in steering the guide catheter body 102 through the tortuous pathway "A". The proximal portion of the catheter body 102 encloses delivery lumen 114 extending between a delivery lumen entry port at catheter body proximal end 112 within hub 110 and a delivery lumen exit port 134 disposed along the catheter body proximal to the catheter body distal end 118.

To some degree, the disposition of the delivery lumen 114 and a guide lumen 116 extending side-by-side through a circular catheter body 108 will cause the catheter body 102 to preferentially bend in a direction that is transverse to a geometric axis plane AP (shown in FIG. 5) defined by the parallel lumen axes, particularly when advanced through a tortuous pathway "A". In one approach, the catheter body 102 is shaped to overcome that preferential bending tendency to cause the catheter body 102 to preferentially bend in a fashion to bias the delivery lumen exit port 134 toward the vessel wall. Various shaping techniques and shapes are set forth in the preferred embodiments.

Figure 5:
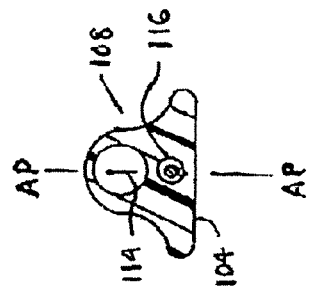
FIG. 5 is a cross-section view taken along lines 5-5 in FIG. 4 depicting the shape of at least a portion of the catheter body to preferentially urge the delivery catheter lumen exit port toward the vessel wall and the underlying heart and away from the pericardium and pericardial space during advancement of the guide catheter body through coronary vessels depicted in FIG. 1.
Figure 4:
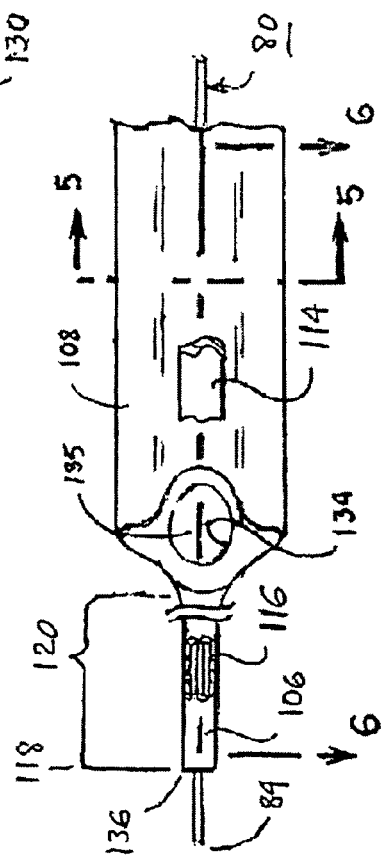
FIG. 4 is a partial view of a distal segment of the catheter body of FIG. 3 depicting the leader, the delivery lumen exit port, and the guide wire extending from the guide lumen exit port.

The proximal portion 108 is extruded into the shape depicted in FIG. 5, for example, to have a non-circular cross-section and to incorporate guide lumen 116 and delivery lumen 114. The non-circular cross section can be achieved by a flange 104 presenting a flattened surface extending along at least a segment of the proximal portion 108 in a plane orthogonal or transverse to the axis plane AP defined by the axes of the delivery and guide lumens 114 and 116. The flattened surface of flange 104 has an extended width, for example, that encourages bending of the proximal portion 108 in one direction in the fashion of a belt. The flattened surface of flange 104 can be formed alongside the guide lumen 116 as shown in FIG. 5 or can be formed alongside the delivery lumen 114. Or the catheter body can be shaped to have two generally parallel flat surfaces that are generally orthogonal to the plane defined by the axes of the delivery and guide lumens 114 and 116. The flange 104 need not extend the full length of the proximal portion 108 of the catheter body 102 but may be present in a segment thereof that would be expected to be advanced, in use, into a coronary blood vessel.

The catheter body 102 is reduced in cross-section area diameter in the distal leader 120 extending between the delivery lumen exit port 134 and the guide lumen exit port 136. The distal leader 120 can be tubular in cross-section and tapered distally to facilitate advancement over the guide wire 80 extending through the guide lumen 116. Consequently, the small diameter leader 120 can be advanced readily over guide wire 80 through twists and turns of the tortuous pathway and thereby guides the advance of the larger cross-section proximal segment 108 of the catheter body 102. The small diameter leader 120 can also be advanced deeply into narrow pathways or passages to dispose the more proximal delivery lumen exit port 134 at a desired implantation site. The flattened surface 104 encourages bending of the proximal portion 108 to track the contours of the heart and dispose the delivery lumen exit port 134 aimed toward the heart. The leader 120 can be straight or have one or more preformed bend along the length thereof.

Then, as shown in FIG. 6, the fixation helix 25 can be advanced out of the delivery lumen exit port 134 extending away from the axis of the delivery lumen 114 and toward the heart. The sharpened tip 251 of the fixation helix 25 can then be advanced, as the lead connector assembly is rotated, through the vessel wall and into the underlying myocardium. Fixation is achieved as the fixation helix 25 is screwed into the myocardium.

FIG. 6 also illustrates a further form of shaping of a segment of the catheter body 102 to bias the delivery lumen exit port 134 toward the vessel wall as the fixation helix 25 is advanced out of the delivery lumen exit port 134. The distal end of the delivery lumen is curved into a guide bend 135 just proximal to the delivery lumen exit port 134 so that the sharpened tip 251 extends toward the vessel wall as the fixation helix 25 is advanced out of the delivery lumen exit port 134.

The hub 110 (FIG. 3) coupled to the guide catheter proximal end 112 can take the form of the hub disclosed in co-pending U.S. application Ser. No. 10/319,245. The hub 110 is advantageously formed with a hub delivery lumen mating to the delivery lumen proximal end opening and axially aligned with the catheter body delivery lumen 114. The hub delivery lumen extends through the hemostasis valve 140 and a hub guide lumen defined by a hub guide tube 122 extending through a side extension 132 of the hub 110.

The hemostasis valve 140 includes a proximal rotating closure knob 142, an intermediate side port (extension hose and stopcock not shown) 144 and a distal rotating locking collar (for securing valve to luer hub fitting) 146 that is press fit onto the hub 110. The knob 142 and side port 144 and collar 146 are used in the fashion of a standard hemostasis valve manufactured by numerous suppliers to shut off the flow and to lock the lead or other catheter in relation to the catheter body. The valve 140 provides a lead insertion lumen axially aligned with the hub delivery lumen 148 so that a cardiac lead 20 of the types described above can be inserted therethrough and into the catheter body delivery lumen 114.

The hub guide tube 122 extends in an arcuate path through window 150 and the side extension 132 that can also be coupled with a Luer type hemostasis valve to seal around the guide wire 80 in a manner well known in the art. The hub 110 and the catheter body 102, particularly the proximal portion 108, are formed to be slittable along the lengths thereof to exposed the aligned hub and catheter body delivery lumens and release the lead body of the cardiac lead 20 in a manner described in the above-referenced '346 and '433 patents. An enlarged, relatively flat pad or paddle 130 is formed extending away from the hemostasis valve 140 and the hub guide tube 122 that can be gripped on either side by the fingers to assist in holding and manipulating the hub 110 during adjustment of the hemostasis valve 140 and advancement of the catheter body assembly of the cardiac lead 20 and catheter body 102 through the tortuous pathway over the guide wire 80.

The guide wire 80 may have an outer diameter in the range of 0.014 to 0.016 inches. The guide wire 80 can be a guide wire that is either introduced by itself or is introduced through a separate, small diameter introducer, e.g., a COOK® Road-Runner® Extra Support guide wire having an outer diameter of 0.018 inches (0.49 mm). The guide wire 80 can also be a deflectable or steerable guide wire of the type disclosed in commonly assigned U.S. Pat. No. 4,815,478, for example.

The bilumen guide catheter 100 depicted in FIGS. 3-6 can also be advanced through the tortuous pathway "A" of FIG. 1 employing a stiffening stylet or steerable stylet substituted for guide wire 80 inserted into guide lumen 116 to stiffen and selectively bend the distal leader 120 to during such advancement. In this variation, the guide lumen exit port is preferably closed or blocked by a block 138 to inhibit the ingress of blood and fluids.

A typical stylet includes a stainless steel wire extending between a proximal stylet wire handle and stylet wire distal end. The stylet wire is adapted to be advanced through the hub guide lumen 125 and the catheter guide lumen 116 from outside the patient's body to abut the stylet distal end against the blockage 138 at the catheter body distal end 118. The stylet wire may have a stylet diameter of about 0.012 to 0.016 inches. The stylet may be a steerable stylet, e.g., the MEDTRONIC® Model 9210 steerable stylet or a steerable stylet of the types disclosed in commonly assigned U.S. Pat. Nos. 5,873,842 and 6,146,338.

Certain embodiments of the bilumen catheter body 102 can advantageously be formed by extrusion of a single polymeric material without the necessity of reinforcement or changing material characteristics along its length. The bilumen catheter body 102 can be extruded from medical grade thermoplastic resins of 35D Shore durometer, for example, to form the delivery tube 104 joined to a guide tube 106 at the elongated junction 108. A radiopaque marker band can be incorporated at the catheter body distal end 118 at the distal tip of the distal leader 120.

The proximal portion 108 can be extruded from medical grade thermoplastic resins of 70D-75D Shore durometer, for example, and the distal leader 120 can be extruded from medical grade thermoplastic resins of 75A-35D Shore durometer, for example. The durometer of the proximal portion 108 is therefore lower than the durometer of the distal leader 120. The higher durometer of the distal leader 120 enables it to be formed having a thin sidewall so that the distal leader 120 can be made smaller in diameter while providing a suitable guide lumen diameter to track a guide wire or receive a stylet or to be directed into smaller diameter blood vessels or other body tracts. The harder surface of the higher durometer material tends to have lower contact stress and, thus, presents lower friction to the guide wire. Moreover, the higher durometer distal leader 120 can be shaped to have a pre-formed bend or curvature that is assumed upon retraction of the guide wire and assists in urging the delivery lumen exit port 134 toward the heart. The medical grade thermoplastics can be selected from polyether block amide (PEBA), polyamide (PA), polyurethane (PU), polyester (PET), polybutylene terephthalate (PBT), or polyvinyl chloride (PVC). Optimally, the proximal portion 120 can be extruded from one of the group consisting of PEBA, PU, PET or PVC having a relatively low durometer, whereas the smaller diameter distal leader 120 can be extruded from the group consisting of PEBA, PU, PA, PET, PBT or PVC having a relatively higher durometer.

In addition to the radiopaque marker band, an atraumatic soft tip can be applied at the catheter body distal end 118. The soft tip can be formed of a polyurethane, e.g., TECOFLEX® TT-1074A polyurethane sold by Thermedics Polymer Products, Inc., Woburn, Mass. The polyurethane material can be loaded with a radiopaque material, e.g. Barium sulfate or tungsten powder, to make the resulting molded soft tip radiopaque.

The surfaces of delivery lumen 114 and guide lumen 116 may be coated with a lubricant to facilitate advancement of a cardiac lead 20 or other instrument through the delivery lumen 114 and the guide wire 80 or stylet wire or other instrument through the guide lumen 116. The exterior surface of a distal portion of the catheter body 102 including the distal leader 120 can also be coated with the lubricant to facilitate advancement of the distal leader 120 through the tortuous pathway. Suitable biocompatible lubricating coatings include a silicone-based lubricant, e.g., a silicone oil, or a reactive silicone lubricant, e.g., MDX4-4159 silicone lubricant available from Dow Chemical Co., Midland, Mich. Other suitable biocompatible lubricating coatings include hydrophilic slip coating materials, e.g., polyacrylamide, polyvinylpyrrolidone, hyaluronic acid, or polyethylene oxide.

Figure 7:
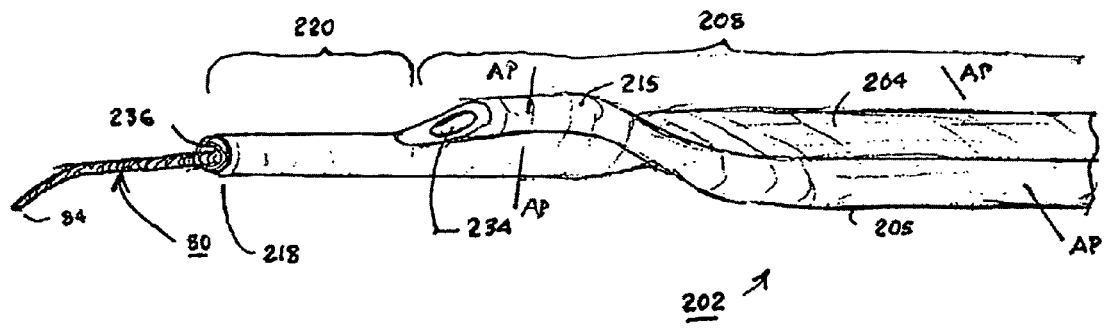
FIG. 7 is a partial perspective view of a further embodiment of a bi-lumen catheter body adapted to be combined with a hub of the type depicted in FIG. 3, the catheter body shaped to optimally dispose the delivery lumen exit port toward the heart.
Figure 8:
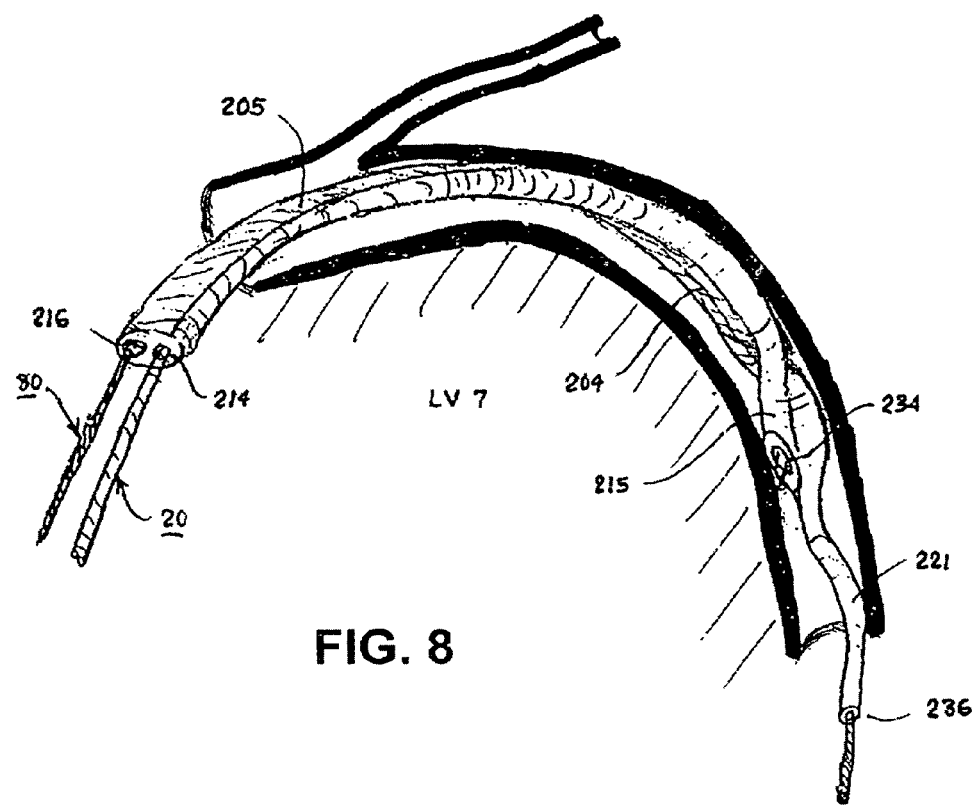
FIG. 8 is a partial schematic illustration of the disposition of the delivery lumen exit port of the catheter body of FIG. 7 toward the heart to affix the fixation helix of the cardiac lead of FIG. 2 when the guide catheter body is advanced through the tortuous pathway from outside the patient's body to the implantation sites illustrated in FIG. 1.

Referring to FIGS. 7 and 8, a further embodiment of the guide catheter 100, particularly having a further catheter body 202 including a proximal portion 208 and a distal leader 220, is shown. In this embodiment, the proximal portion 208 of catheter body 202 is extruded into a substantially oval or rectangular cross-section shape having opposed major, substantially flat, sides 204 and 205. The delivery lumen 214 and guide lumen 216 extend side-by-side through the proximal portion 208 between the major sides 204 and 205. The parallel axes of the delivery lumen 214 and guide lumen 216 define a geometric axis plane AP, and the major sides 204 and 205 extend substantially in parallel with the axis plane AP. A short distal segment of the delivery lumen 214 is shifted out of side-by-side alignment with a corresponding segment of the guide lumen 216 to dispose the delivery lumen exit port 234 above or alongside the major side 204. The axis plane AP is in effect twisted from a first orientation prevailing in the proximal segment of the proximal portion 208 into a second orientation near the delivery lumen exit port 234 (as shown in FIGS. 7 and 8) that is substantially transverse to the first orientation. The distal end of the delivery lumen 214 can be shaped with a curved guide bend 135 of the type depicted in FIG. 6.

As shown in FIG. 8, the opposed major sides 204 and 205 tend to cause the catheter body 202 to advance through the coronary vasculature over the guide tool, e.g., the guide wire 80, within the guide lumen 216 with the delivery lumen exit port 234 disposed toward the heart. A curve 221 is preferably pre-formed in the distal leader 220 extending away from the major side 205 that tends to offset the shift of the delivery lumen exit port 234 into alignment with the major side 204 and to dispose the delivery lumen exit port 234 toward the heart, particularly the myocardium of the LV 7 as also shown in FIG. 8.

The delivery lumen 214 and the guide lumen 216 can constitute co-extruded tubes of the materials described above. The connection between the co-extruded tubes can be severed along the length of the distal segment of the delivery lumen 214. The distal ends of the co-extruded tubes can be cut to length to form the distal leader 220 and to dispose a short segment of the tube surrounding the delivery lumen 214 over a proximal segment of the tube surrounding the guide lumen 216. Or, a distal segment of the proximal portion 208 and the distal leader 220 can be molded as a separate assembly that is adhered to a distal end of the substantially rectangular cross-section extrusion to form the catheter body 202.

A jacket 240 of flat metal or plastic filaments may be braided over the outer surface of the proximal portion 208 of the catheter body 202 that further assists in causing the catheter body to preferentially bend to bias the delivery lumen exit port 234 toward the heart. A thin coating of elastomeric material can be fitted over the jacket 240 to make its exterior surface smooth.

Figure 9:
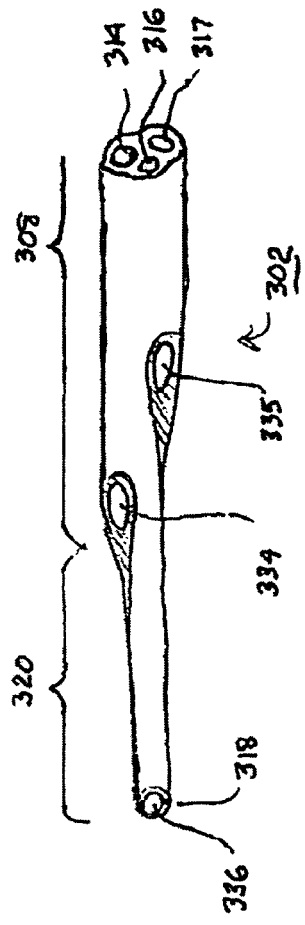
FIG. 9 is a partial plan view of a multi-lumen catheter body having at least two delivery lumens that is adapted to be substituted for the catheter body of the guide catheter of FIG. 3, with suitable modification of the hub.
Figure 10:
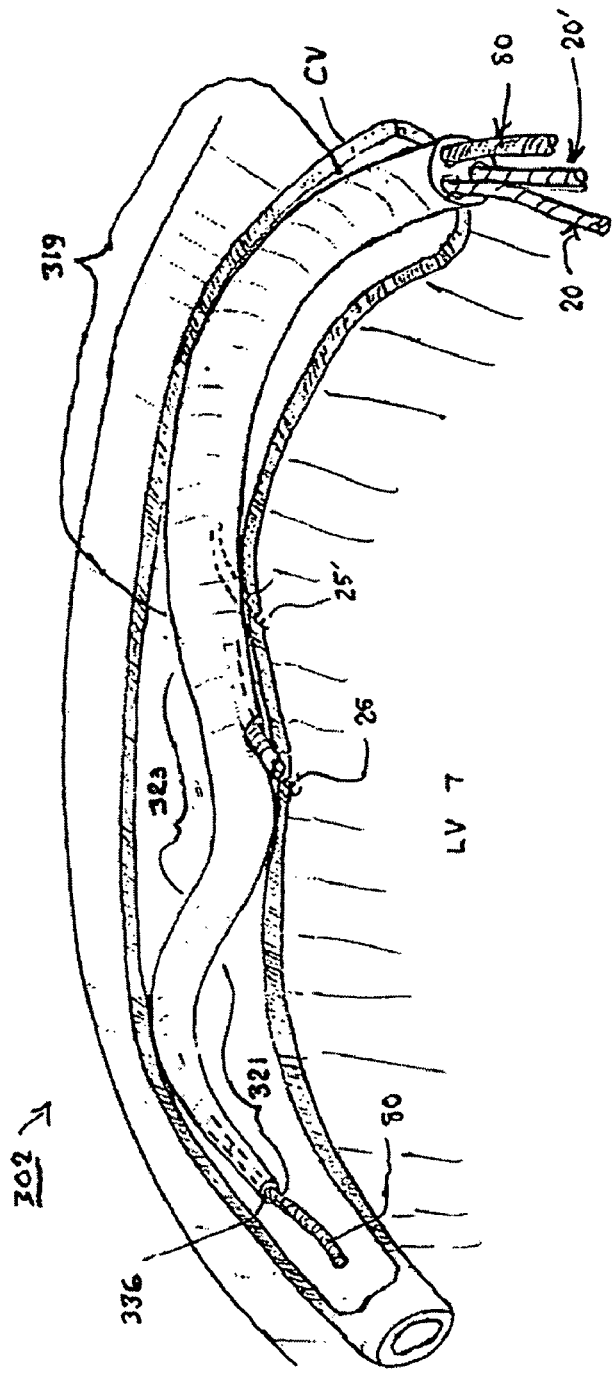
FIG. 10 is a partial schematic illustration of the disposition of the delivery lumen exit ports of the catheter body of FIG. 9 toward the heart to affix the fixation helices of two cardiac leads of FIG. 2 when the guide catheter body is advanced through the tortuous pathway from outside the patient's body to the implantation sites illustrated in FIG. 1.
Figure 11:
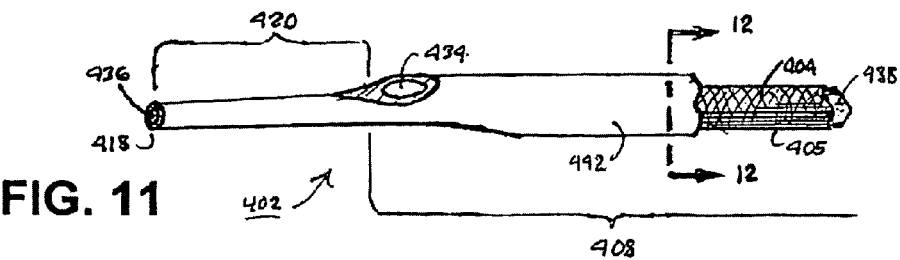
FIG. 11 is a partial perspective view of a further embodiment of a bi-lumen catheter body adapted to be combined with a hub of the type depicted in FIG. 3, the catheter body shaped to optimally dispose the delivery lumen exit port toward the heart.

Referring to FIGS. 9 and 10, a still further embodiment of the guide catheter 100, particularly a further catheter body 302 having at least one further lumen, is shown. In particular, an additional delivery lumen 317 is provided in the catheter body proximal portion 308 that terminates in a further delivery lumen exit port 335. The proximal portion 308 of catheter body 302 is relatively cylindrical to accommodate three lumens 314, 316 and 317. However, shaping of the catheter body 302 to urge the delivery lumen exit ports 334 and 335 toward the heart is accomplished by shapes formed in segments of the proximal and distal portions 308 and 320 that collectively have a shallow "S" shape including pre-formed bends 319, 321 and 323 as shown in FIG. 10.

Figure 12:
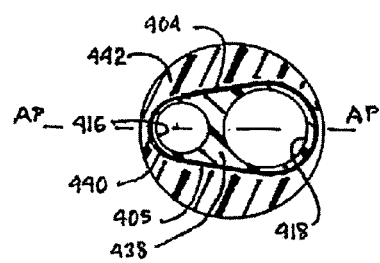
FIG. 12 is a cross-section view taken along lines 12-12 of FIG. 11 depicting one form of internal shaping of the catheter body proximal portion.
Figure 14:
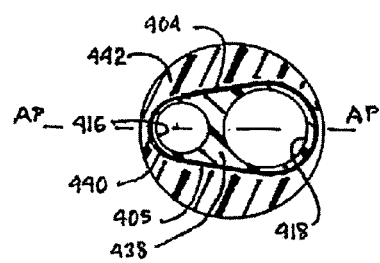
FIG. 14 is a cross-section view taken along lines 12-12 of FIG. 11 depicting a further form of internal shaping of the catheter body proximal portion.
Figure 13:
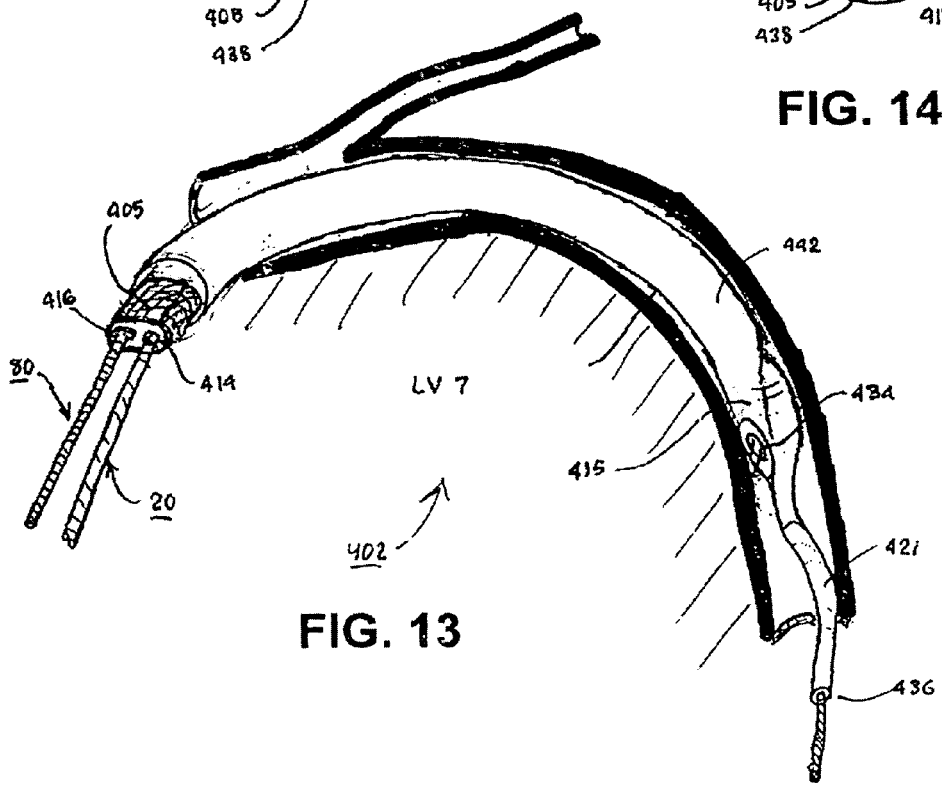
FIG. 13 is a partial schematic illustration of the disposition of the delivery lumen exit port of the catheter body of FIG. 11 toward the heart to affix the fixation helix of the cardiac lead of FIG. 2 when the guide catheter body is advanced through the tortuous pathway from outside the patient's body to the implantation sites illustrated in FIG. 1.

Referring to FIGS. 11-14, a still further embodiment of the guide catheter 100, particularly a further catheter body 402 having an internal shaping structure, is depicted. In this embodiment, the proximal portion 408 of catheter body 402 is formed of a generally cylindrical outer sheath 442 that encloses a generally oval or rectangular or triangular cross-section, bitumen tube 438 having opposed major sides 404 and 405. A delivery lumen 414 and guide lumen 416 extend side-by-side through the tube 438 in proximal portion 408 between the major sides 404 and 405. Two examples of the cross section of bitumen tube 438 are shown in FIGS. 12 and 14 where the major sides 404 and 405 are spaced from and extend substantially parallel to the axis plane AP.

A jacket 440 of flat metal or plastic filaments may be braided over the outer surface of the tube 438 in proximal portion 208 of the catheter body 202 that further assists in causing the catheter body 202 to preferentially bend to bias the delivery lumen exit port 234 toward the heart. In this embodiment, the generally cylindrical outer sheath 442 is formed over the jacket 440 to make the proximal portion 408 of catheter body 402 generally cylindrical.

A short distal segment of the delivery lumen 414 is shifted out of side-by-side alignment with a corresponding segment of the guide lumen 416 to dispose the delivery lumen exit port 434 above or alongside the flat side 404 in the manner described above with respect to the embodiment of FIGS. 7 and 8. The distal end of the delivery lumen 414 can be shaped with a curve like guide bend 135 depicted in FIG. 6.

In this way, the shape of the jacket 440 tends to cause the catheter body 402 to advance through the coronary vasculature over the guide tool, e.g., the guide wire 80, within the guide lumen 416 with the delivery lumen exit port 434 disposed or biased toward the heart. A curve 421 is preferably pre-formed in the distal segment 420 extending away from the flat side 405 that tends to offset the shift of the delivery lumen exit port 434 into alignment with the flat side 404 and to dispose the delivery lumen exit port 434 toward the heart, particularly the myocardium of the LV 7 as also shown in FIG. 12.

These embodiments of bitumen and multi-lumen guide catheters 100 can be employed in a variety of procedures for introducing cardiac leads into coronary veins of the heart, e.g., deep in the cardiac veins descending from the coronary sinus accessed transvenously and through the coronary sinus as illustrated in FIG. 2, to lodge the distal pace/sense electrode in relation to the left ventricle. The guide catheters 100 can also be employed to fix a pace/sense electrode at certain particular sites in a heart chamber, e.g., the right ventricular outflow tract.

Further instruments or diagnostic fluids can be selectively advanced through the delivery lumen and/or the guide lumen to facilitate identification or advancement of the catheter body distal end to the implantation site preceding the advancement of the cardiac lead through the delivery lumen.

The guide catheter having an open guide lumen exit port can advantageously be used to perform other functions, e.g., to facilitate blocking of a cardiac vessel employing a balloon catheter so that radiopaque diagnostic fluid can be introduced into the cardiac vessel to visualize the cardiac vessel in an angiographic procedure in order to identify a suitable implantation site.

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiments without departing from the spirit and scope of the claims. The above described implementations are simply those presently preferred or contemplated by the inventor, and are not to be taken as limiting the present invention to the disclosed embodiments. It is therefore to be understood, that within the scope of the appended claims, the invention may be practiced otherwise than as specifically described without actually departing from the spirit and scope of the present invention.

What is claimed is:

1. A guide catheter for introducing a cardiac lead having a distal fixation mechanism through a pathway from an incision to an implantation site relative to a heart chamber, comprising:

an elongated catheter body extending between a catheter body proximal end and a catheter body distal end, the catheter body having a catheter body sidewall and comprising a proximal portion and a distal leader extending distally from a distal end of the proximal portion;

the catheter body sidewall enclosing a guide lumen having a guide lumen axis and extending between a guide lumen entry port and the catheter body distal end, the guide lumen diameter sized to receive a guide tool inserted therein to aid in steering the guide catheter body through the pathway;

the proximal portion of the catheter body sidewall enclosing a delivery lumen having a delivery lumen axis and extending between a delivery lumen entry port and a delivery lumen exit port through the catheter body sidewall proximal to the distal leader;

the delivery lumen axis and the guide lumen axis extending in a side-by-side manner along a first segment of the proximal portion and defining a first geometric axis plane; and the proximal portion of the catheter body sidewall having a cross-sectional shape comprising a first substantially flat major side extending along a second segment of the proximal portion of the catheter body in a plane that is transverse to the first geometric axis plane to cause the proximal portion of the catheter body to preferentially bend as the catheter body tracks a contour of the heart, the catheter body preferentially bending in a direction that the delivery lumen exit port is oriented to thereby bias the delivery lumen exit port toward the heart during advancement through the pathway to facilitate passage of the fixation mechanism of the cardiac lead through a vessel wall into the myocardium;

wherein the first segment is a distal segment of the proximal portion extending to the delivery lumen exit port;

the delivery lumen axis and the guide lumen axis extending in a side-by-side manner along a third segment of the proximal portion, the third segment proximal to the first segment;

the delivery lumen axis and the guide lumen axis extending along the third segment defining a second geometric axis plane transverse to the first geometric axis plane.

2. The guide catheter of claim 1, wherein the delivery lumen includes a delivery lumen diameter sized to receive the cardiac lead having a lead body enclosing a lead conductor and extending between a proximal lead connector element and a distal electrode to enable introduction of the cardiac lead through the pathway to the implantation site.

3. The guide catheter of claim 1, wherein the cardiac lead fixation mechanism is one of a fixation helix adapted to be screwed through the vessel wall into the myocardium or a hook or a prong adapted to be extended through the vessel wall into the myocardium.

4. The guide catheter of claim 1, wherein the guide lumen terminates in a guide lumen exit port in the distal leader formed to receive a guide tool inserted into the guide lumen as the guide catheter is advanced over the guide tool.

5. The guide catheter of claim 1, wherein the first and third segments together extend a full length of the proximal portion, wherein the proximal portion of the catheter body preferentially bends in a preferential bending direction substantially transverse to the first geometric axis plane defined by the delivery lumen axis and the guide lumen axis.

6. The guide catheter of claim 5, wherein the distal end of the delivery lumen is curved into a guide bend proximal to the delivery lumen exit port that deflects the distal fixation mechanism of the cardiac lead out of the first geometric axis plane and toward the preferential bending direction.

7. The guide catheter of claim 1, wherein the distal end of the delivery lumen includes a curved portion proximal to the delivery lumen exit port that deflects the distal fixation mechanism of the cardiac lead out of the first geometric axis plane and toward the preferential bending direction.

8. The guide catheter of claim 1, wherein the catheter body sidewall includes a flange extending transverse to the first geometric axis plane to form the first substantially flat surface that enables the preferential bending of the catheter body substantially transverse to the first geometric axis plane.

9. The guide catheter of claim 8, wherein the distal end of the delivery lumen includes a curved portion proximal to the delivery lumen exit port that deflects the distal fixation mechanism of the cardiac lead out of the first geometric axis plane and toward the preferential bending direction.

10. The guide catheter of claim 1 wherein a distal segment of the delivery lumen is shifted out of the side-by-side alignment with a corresponding segment of the guide lumen to position the delivery lumen exit port along the first substantially flat major side.

11. The guide catheter of claim 1 wherein the cross-sectional shape comprises a second substantially flat major side extending transverse to the first geometric axis plane orientation.

12. The guide catheter of claim 11 wherein the second substantially flat major side being substantially parallel to the first substantially flat major side.

13. The guide catheter of claim 1 further comprising a cylindrical outer sheath enclosing the catheter body sidewall.

14. The guide catheter of claim 1 further comprising a jacket of flat filaments braided over an outer surface of the catheter body sidewall.

15. The guide catheter of claim 1 wherein the first segment and the second segment overlap.

16. A guide catheter for introducing a cardiac lead having a distal fixation mechanism through a pathway from an incision to an implantation site relative to a heart chamber, comprising:
  an elongated catheter body extending between a catheter body proximal end and a catheter body distal end, the catheter body having a catheter body sidewall and comprising a proximal portion and a distal leader extending distally from a distal end of the proximal portion;
  the catheter body sidewall enclosing a guide lumen having a guide lumen axis and extending between a guide lumen entry port and the catheter body distal end, the guide lumen diameter sized to receive a guide tool inserted therein to aid in steering the guide catheter body through the pathway;
  the proximal portion of the catheter body sidewall enclosing a delivery lumen having a delivery lumen axis and extending between a delivery lumen entry port and a delivery lumen exit port through the catheter body sidewall proximal to the catheter body distal end,
  wherein the delivery lumen and the guide lumen extend in side-by-side relation through a first segment of the proximal portion and define a first geometric axis plane,
  the delivery lumen shifted out of the side-by-side relation in a distal segment of the proximal portion to orient the delivery lumen exit port in a direction transverse to the first geometric axis plane,
  the catheter body sidewall comprising a cross-sectional shape having at least one substantially flat major side that extends along at least a segment of the proximal portion of the catheter body in a plane that is parallel to the first geometric axis plane thereby causing the catheter proximal portion to bend in the direction of the delivery lumen exit port as the catheter body tracks a contour of the heart and thereby bias the delivery lumen exit port toward a blood vessel wall at the implantation site;
  wherein the first segment is a distal segment of the proximal portion extending to the delivery lumen exit port;
  the delivery lumen axis and the guide lumen axis extending in a side-by-side manner along a second segment of the proximal portion, the second segment proximal to the first segment;
  the delivery lumen axis and the guide lumen axis extending along the second segment defining a second geometric axis plane transverse to the first geometric axis plane.

17. The guide catheter of claim 16, wherein the distal end of the delivery lumen includes a curved portion forming a guide bend proximal to the delivery lumen exit port that deflects the distal fixation mechanism of the cardiac lead out of the axis plane and toward the preferential bending direction.

18. The guide catheter of claim 16, further comprising:
  an inner tube positioned along the first segment of the proximal portion of the guide catheter body enclosing the guide lumen and delivery lumen in side-by-side relation that is shaped to have at least one major side that extends along at least a segment of the proximal portion of the catheter body substantially parallel with the first geometric axis plane, the at least one major side generating the preferential bending and biasing the delivery lumen exit port toward the heart during advancement of the guide catheter through the pathway to facilitate passage of the fixation mechanism of the cardiac lead through the vessel wall into the myocardium; and
  an outer sheath formed over the inner tube having a substantially cylindrical sheath outer surface.

19. The guide catheter of claim 18 wherein the inner tube comprises filaments braided over an outer surface of the first segment of the proximal portion of the guide catheter body, the braided filaments formed to assist in causing the catheter body to preferentially bend in the preferential bending direction.

20. The guide catheter of claim 16, wherein the delivery lumen has a delivery lumen diameter sized to receive the cardiac lead to enable introduction of the cardiac lead through the pathway to the implantation site.

21. The guide catheter of claim 16, wherein the guide lumen terminates in a guide lumen exit port in the distal leader enabling advancement of the guide catheter over a guide tool inserted into the guide lumen.

22. The guide catheter of claim 16, wherein the guide tool comprises one of a guidewire, a stiffening stylet, and a steerable stylet.

23. A guide catheter for introducing a cardiac lead having a distal fixation mechanism through a pathway from an incision to an implantation site relative to a heart chamber, comprising:
  an elongated catheter body extending between a catheter body proximal end and a catheter body distal end, the catheter body having a catheter body sidewall and comprising a proximal portion and a distal leader extending distally from a distal end of the proximal portion;
  the catheter body sidewall enclosing a guide lumen having a guide lumen axis and extending between a guide lumen entry port and the catheter body distal end, the guide lumen diameter sized to receive a guide tool inserted therein to aid in steering the guide catheter body through the pathway; and
  the proximal portion of the catheter body sidewall enclosing a delivery lumen having a delivery lumen axis and extending between a delivery lumen entry port and a delivery lumen exit port through the catheter body sidewall proximal to the catheter body distal end;
  the guide lumen axis and the delivery lumen axis extending in a side-by-side manner along a first segment of the proximal portion and defining a first geometric axis plane;
  the proximal portion of the catheter body sidewall having a cross-sectional shape comprising at least one substantially flat major side that extends along at least a segment of the proximal portion of the catheter body in a plane that is transverse to the first geometric axis plane to cause the proximal portion of the catheter body to preferentially bend as the catheter body tracks a contour of the heart, the catheter body preferentially bending in a direction that the delivery lumen exit port is oriented, the catheter body sidewall comprising a curved inner wall forming a guide bend just proximal to the delivery lumen exit port to bias the delivery lumen exit port away from the guide lumen and toward the heart during advancement through the pathway to facilitate passage of the fixation mechanism of the cardiac lead through a vessel wall into the myocardium;

wherein the first segment is a distal segment of the proximal portion extending to the delivery lumen exit port;

the delivery lumen axis and the guide lumen axis extending in a side-by-side manner along a second segment of the proximal portion, the second segment proximal to the first segment;

the delivery lumen axis and the guide lumen axis extending along the second segment defining a second geometric axis plane transverse to the first geometric axis plane.

* * * * *